United States Patent [19]

Thomas

[11] 4,382,083

[45] May 3, 1983

[54] THERAPEUTIC METHOD FOR TREATING BLOOD-CLOTTING DEFECTS WITH FACTOR VIIA

[75] Inventor: William R. Thomas, Laguna Niguel, Calif.

[73] Assignee: Baxter Travenol Laboratories, Inc., Deerfield, Ill.

[21] Appl. No.: 277,469

[22] Filed: Jun. 25, 1981

[51] Int. Cl.³ .............................................. A61K 35/14
[52] U.S. Cl. .................................................. 424/101
[58] Field of Search ...................... 424/101; 260/112 R

[56] References Cited

U.S. PATENT DOCUMENTS 3,560,475 7/1976 Fekete et al. .
4,160,025 3/1975 Eibl et al. .

OTHER PUBLICATIONS

Broze et al.—Chem. Abst. vol. 92 (1980) pp. 144, 161a.
Suomela et al., "Vox Sang." 33:37-50 (1977).
Vermylen et al. "Brit. J. Haematology" 38:235-242 (1978).
Kelly et al., "J. American Med. Assoc." 236(18):2061-2064 (1976).
Stenbjerg et al. "Acta. Med. Scand." 203:471-476 (1978).
Fekete et al., "XIV International Congress of Hematology" (1972).
Penner et al. "Sem. Thromb. Hemostas," 1:386-399 (1975).
Blatt et al. "Thrombos. Haemostas. (Stuttg.)" 38:514-522 (1977).
Buchanan et al. "Pediatrics" 62(5):767-774 (1978).
Kurczynski et al. "New England J. Med." 291(4):164-167 (1974).
Stenbjerg et al. "Scand. J. Haematol." 18:421-426 (1977).
Tishkoff, "New England J. Med." 292:754-755 (1975).
Sakuragawa et al. "Thrombosis Res." 1:315-318 (1977).
Seligsohn et al. "Blood" 53(5):828-837 (1979).
Kingdon et al. "Thrombos. Diathes. Haemorrh. (Stuttg.)" 33:617-631 (1975).
Pepper et al. "Brit. J. Haematology" 36:573-583 (1977).
Fekete et al., American Society of Hematology Abstract 171 (1969).
White et al. "Blood" 49(2):159-170 (1977).
Ratnoff, "Ann. Internal Med." 81(6):852-853 (1974).
Exner et al. "Biomedicine (Express)" 27(2):62-65 (1977).
Gjonnaess, "Thrombos. Diathes. Haemorrh. (Stuttg.)" 28:194-205 (1972).
Laake et al. "Thrombosis Res." 5:759-772 (1974).
Kisiel et al., "Biochemistry" 16:4189-4194 (1977).
Kisiel et al., "Biochemistry" 14:4928-4934 (1975).
Nemerson et al., "J. Lab. Clin. Med." 83(2):301-303 (1974).
Broze, Jr., et al., "J. Biol. Chem." V255(4):1242-1247 (1980).
Mariani, G., et al., "Thromb. Haemost." 42:365 (1979).
Seligsoh, U. et al., "Blood" V52(5):978-988 (1978).
Radcliffe, R. et al., "J. Biol. Chem." V250(2):388-395 (1975).
Price, D. A. et al., "Aust. NZ J. Med." 7(3):286-290 (1977).
Hess et al., "Abstracts of VI Int. Cong. Throm. Haem." p. 188 (1977).

*Primary Examiner*—Sam Rosen
*Attorney, Agent, or Firm*—Paul Flattery; Lawrence Flynn; Max D. Hensley

[57] ABSTRACT

Patients having a clotting factor defect can be successfully treated by the administration of a composition containing effective hemostatic amounts of factor VIIa. Preferably, the factor VIIa is substantially free of factors IXa and Xa. Procedures for preparing the above therapeutic compositions are also described.

19 Claims, No Drawings

THERAPEUTIC METHOD FOR TREATING BLOOD-CLOTTING DEFECTS WITH FACTOR VIIA

BACKGROUND OF THE INVENTION

This invention relates to methods for treating patients having deficiencies or inhibitors of blood clotting factors, particularly factor VIII (antihemophilic factor, AHF).

Blood coagulation is an exceedingly complex process. The interaction of various blood components which eventually gives rise to a fibrin clot has been compared to a cascade of steps, each of which is dependent upon and regulated by preceding and following steps. Generally, the blood components which take part in the coagulation cascade are either proenzymes or enzyme modulators. The proenzymes are enzymatically inactive proteins which are converted to proteolytic enzymes by the action of an "activator", generally another proteolytic enzyme produced at an earlier stage in the coagulation cascade. Coagulation factors which have undergone such a conversion are hereafter defined as activated factors, and designated by the lower case postscript "a" while the proenzymes are referred to as precursor clotting factors.

The enzyme modulators are principally cofactors such as calcium ions or nonenzyme proteins and most are essential if the enzymes are to exhibit any catalytic activity at all. Such modulators are to be distinguished from enzyme substrates. Substrates are compounds which are covalently modified by an enzyme while modulators or cofactors merely bind to the enzyme without undergoing a change in structure.

Proenzymes are key components in the blood coagulation cascade. They constitute a reservoir to supply the needs of the clotting cascade, being activated to the enzymatically functional form as required. The extent of activation and the activity of the enzymes are controlled by the modulators.

Factor VII is one of these proenzymes. Factor VII participates in the extrinsic pathway of blood coagulation by converting factor X to Xa in the presence of tissue factor. Factor Xa in turn then converts prothrombin to thrombin in the presence of the cofactors factor V, calcium ions and phospholipid. Recent evidence indicates that factor VIIa may participate in the intrinsic clotting pathway as well.

Bovine factor VII has been isolated and characterized (Kisiel and Davie, "Biochemistry" 14 (22): 4928-4934 [1975]). The factor VII purified by these authors was homogeneous when examined by gel electrophoresis in the presence of sodium dodecyl sulfate, exhibited less than 0.001 Ortho units of prothrombin/ml and undetectable levels of factors IX and X when assayed at 0.5 mg protein/ml concentration. Since Factor VII activity losses are high at low protein concentrations, 1 mg/ml of bovine serum albumin was included in factor VII diluents as a stabilizer.

Bovine factor VII is a single-chain glycoprotein of approximately 50,000 daltons. It is converted to a two chain disulfide-linked protein by factor Xa in the presence of calcium ions and phospholipids, or by thrombin or factor XIIa without cofactors. An increase in factor VII activity of about 10 to 100 fold as measured in a one-stage coagulation assay is associated with the conversion to the two chain form.

Human factor VII has also been purified and characterized (Broze and Majeurs, "J. Biol. Chem." 1242-1247 [1780]. This method yields factor VII which, like the bovine product obtained by Kisiel and Davie, was without detectable activity by coagulation assay and did not contain detectable factors X, IX or II. The final preparation contained 2.3 units of factor VII/$\mu$g of protein. The human factor VII is 55-85% homologous with the bovine protein and shows many other characteristics in common with bovine factor VII. Like bovine factor VIIa, it is converted to a two chain form upon activation, apparently via proteolytic cleavage. The activity increase upon activation to the two chain from is 20-25 fold. This two chain form will be synonymous hereinafter with factor VIIa.

Factor VIIa previously has not been employed to the applicant's knowledge to treat patients with clotting inhibitors or deficiencies. However, factor VIIa is known to be present in activated prothrombin complex (PCC), a complex mixture of activated and unactivated clotting enzymes used to treat patients having inhibitors of factor VIII.

The therapeutically effective substances in activated prothrombin complexes have been speculated to be one or more of factors IXa, Xa, XIa, XIIa, VIIa, Xa dimer, Xa-prothrombin intermediate binary complex, "large quantities" of factor VII, a "modified form" of factor VII, factor VIII inibitor bypassing activity (FEIBA), platelet factor X activator and, to a small degree, thrombin. The overriding theme espoused by the art, however, is that an incomplete understanding exists of the in vivo mechanism of action for activated PCC, and therefore the art has been able to only speculate as to the effective in vivo hemostatic agent or agents in these compositions.

The therapeutic use of activated PCC would be improved by purifying the effective hemostatic agent. This would result in the administration of less extraneous protein to the patient. In addition, the economics of protein fractionation would be enhanced by diverting the unwanted residue from the purification to the manufacture of other therapeutic products.

Accordingly, it is an object of this invention to identify a hemostatic agent in activated PCC that can be isolated and used alone for the therapy of blood clotting deficiencies.

It is a further object to identify such a hemostatic agent having a low potential for adverse thrombosis such as disseminated intravascular coagulation.

It is an additional object to identify such an agent which can be used so as to not stimulate patients to generate clotting factor inhibitors.

These and other objects of the invention will be apparent from the specification as a whole.

SUMMARY OF THE INVENTION

Applicant has found that purified factor VIIa is a hemostatic agent in its own right. It does not require the administration of any other activated or unactivated factor to be therapeutically effective in achieving hemostasis. This was particularly surprising with respect to factors IXa and Xa since the art has speculated frequently that these factors are likely candidates for the hemostatic effect of activated PCC. The effectiveness of factor VIIa was also surprising because the experimental animals were not deficient in factor VII and therefore could presumably have generated all the factor VIIa that would have been needed to correct bleeding.

Accordingly, the method herein comprises administering to a patient having a clotting factor defect such as a deficiency or inhibitor an effective hemostatic amount of a composition in which the sole effective, activated hemostatic agent is factor VIIa.

The factor VIIa to be used in the method of this invention is free of a quantity of activated blood clotting factors which alone would be sufficient to exert an in vivo, clinically hemostatic effect in the experimental dog model described herein. Thus, it is conceivable that the compositions of this invention may contain activated blood clotting factors other than factor VIIa. However, the activity of such contaminant factors will be so low that no clinically detectable hemostatic effect will be observed if the VIIa activity of the contaminated composition is inhibited or physically separated from the contaminants and the contaminants then administered under substantially the same conditions, e.g., infusion rate and concentration, as would have been the case when factor VIIa was present in the contaminated composition. Alternatively, the contaminated composition can be purified free of factor VIIa, e.g. by elelctrophoresis, and the residue assayed for clotting activity in a non-activated partial thromboplastin time test or other general assay for endogenous clotting activity. If the clotting activity as measured by the Nemerson method before and after separation of factor VIIa has decreased more than three times over a control using pure factor VIIa then the composition is deemed to contain a sufficiently low level of contaminant clotting proteases to enable it to be used in this invention.

Hemostatic effect or amount is defined as the cessation of bleeding in a statistically significant number of hemophilia A dogs as described below in Example 1 within about 30 minutes after the infusion of the test sample, which cessation was accompanied with an insignificant drop in hematocrit over a period of 3 hours following infusion.

Such compositions ordinarily will contain less than about 1 unit of factor Xa/ml and less than about 0.001 unit of thrombin/ml. The difference obtained by subtracting total factor IX activity from factor IX precursor activity, which yields an indirect measure of factor IXa, will be no more than about 15 units/ml and is generally less than about 5 units/ml. The unit activities of these activated factors were determined by the methods set forth in copending U.S. patent application Ser. No. 116,187; factor Xa was determined by the chromogenic method described therein.

It is not necessary that any contaminant activated clotting factors be physically separated from the therapeutic composition since they may be inactivated or inhibited in situ. for example by inclusion or antithrombin III and low levels of heparin, on the order of about 1 to 3 units of heparin/$\mu$g factor VIIa. However, it is preferred to purify the factor VIIa, either separating factor VII from residual unactivated clotting factors and then activating, or by purifying factor VIIa following activation. Of the two alternatives, it is preferred to purify factor VII prior to activation. The separated clotting factors such as factors IX and X are more versatile if the option to activate them still remains. Additionally, the activation may be more readily controlled and the quantity of starting material one must deal with is considerably reduced if factor VII is purified prior to activation.

The above discusion has dealt with the presence of activated clotting factors in the therapeutic composition. Unlike the case with activated clotting factors, the unactivated precursor forms of such factors may be present in the compositions up to an amount which results in such dilution of factor VIIa that administration of factor VIIa in a therapeutically effective dose would entail infusion of therapeutically unacceptable amounts of protein. This is quite a high concentration and as a practical matter imposes no limits in the case of typical plasma fractionation products. The amounts of unactivated factors II, VII, IX and X will typically range from about 1-10, 30-250, 0-30 and 1-30 units/ml, respectively. Preferably, the compositions are essentially free of factors IX and II but contain factors VII and/or X in the above concentrations. The unit activities were determined by the methods described in the above-cited U.S. patent application.

Other blood plasma proteins than the activated or unactivated clotting factors may be present in the compositions to be used in the invention herein. Again, contamination with extraneous protein is preferably avoided but is not critical. It is desirable, in fact, to leave some protein in the purified factor VIIa to act as a stabilizer. For example, it is known that albumin stabilizes factor VIIa activity. Generally a protein concentration greater than about 1 mg/ml is satisfactory to achieve factor VII stability although this amount is not critical.

Other physiologically-acceptable stabilizers may be included in the factor VIIa-containing compositions to be used in accordance with this invention. Examples include non-reducing sugars, polysaccharides such as low molecular weight dextrins, polyalcohols such as sorbitol or glycerol, amino acids including glycine, and antioxidants such as bisulfite or ascorbate. The stabilizers are generally present in a concentration of about from 0.1 to 3% weight/volume.

Factor VIIa is useful in treating a variety of clotting factor inhibitors and deficiencies, in particular patients having deficiencies or inhibitors of factors VIII, IX and XI. Patients having inhibitors of factors VIII or IX have been observed. Inhibitors are substances believed to be antibodies against the inhibited factors. These substances interact with the factors, probably by immune binding and steric hindrance, so as to prevent their participation in the clotting mechanism. Inhibitors are a particularly acute problem because inhibitor titers generally increase in response to even larger doses of clotting factor, and thus tend to eventually overcome high dosage therapeutic approaches. This invention has particular applicability in the treatment of factor VIII inhibitors.

Deficiency syndromes exist where the factor itself is lacking, is present in ineffectual concentrations, or is a protein having some antigenic similarities to the clotting moiety but which is substantially nonfunctional in the clotting system. Deficiencies may result from a variety of causes, most commonly of congenital origin or the destruction of clotting factor-producing organs. The most serious clotting factor deficiencies are those of factors VIII, IX and XI, and defects of the clotting mechanism attendant chronic liver disease such as alcoholic cirrhosis and viral hepatitis.

Factor VIIa is preferably administered upon diagnosis of a bleeding episode rather than prophylactically. It should be administered as an aqueous solution by infusion rather than by bolus injection. The activity of factor VIIa in the infusion solution and the dosage of factor VIIa activity will necessarily depend upon the therapeutic circumstances facing the clinician, e.g., severity and location of the bleed and the general condition of the patient.

The activity of factor VIIa in an infusion solution may vary over a wide range and is not critical, although the overall protein concentration in the solution should be maintained to aid in stabilizing the factor. Generally, suitable infusions will contain about from 0.1 to 10.0 μg of factor VII a/ml. Albumin or other stabilizing proteins should be present in the infusion at about from 1 to 5 mg/ml.

Factor VIIa is preferably dosed as the mass of double chain moiety present in the composition to be used. Methods are well known in the art for measuring and distinguishing the mass of one protein in admixture with other proteins. Such techniques include electrophoresis or immunoassay.

A convenient shorthand modification of the mass dose technique is to simply measure the factor VII content of a composition prior to taking steps to activate the proenzyme. Then conditions are selected for activation which have been determined previously with purified factor VII from the same source to yield the maximum increase in factor VIIa activity (expressed factor VII activity). Since the molecular weights of factors VII and VIIa are substantially the same, the mass of factor VIIa will be substantially the same as the starting factor VII. And since it is a given that activation conditions have been maximized, it may be assumed that substantially all factor VII has been converted to factor VIIa.

Alternatively, dosage may be expressed in factor VII units. However, one should first take steps to ensure that the test material is free from substantial contamination by factor VII and non-factor VIIa activated clotting factors, which will interfere in the factor VII clotting assay. The material should be purified substantially free of factor VII because factors VII and VIIa both exhibit the same qualitative activity in the clotting mechanism, even though the activated form is about from 10 to 100 times more active than factor VII. Since the assay is also a clotting assay, it too is incapable of distinguishing factor VII from factor VIIa. Also, since the method is based on the formation of a fibrin clot activated factors such as factor Xa or thrombin, which can generate fibrin as well, will contribute to false positive results. It is not critical to remove the factor VII in activated compositions because factor VIIa is about from 10 to 100 times more active than the proenzyme; any contribution to the assay by factor VII will be swamped by the comparative vigor of factor VIIa in the assay.

The dosage of factor VIIa suitable for deficiency and inhibitor states will depend upon clinical circumstances such as the residual activity of inhibited or deficient clotting factors, the site of the bleed and its magnitude, the general physical condition of the patient and a host of other factors. Thus the dose must be varied by the clinician to arrive at the optimum therapy. This is of course a routine problem faced by physicians in dealing with other therapeutic compositions and should therefore be within the skill of the artisan. Generally a dose of about from 0.1 to 2.5 μg of VIIa per kg of body weight is preferred, with about from 0.1 to 1.5 being most desirable. This dosage range will induce hemostasis within about from 15 to 30 minutes, whereas untreated subjects generally continue to bleed uncontrolably. This range is intended only as a guide to the artisan and is not to be construed as appropriate for each and every therapeutic situation.

The frequency of dosage will depend upon the clinician's judgment as well. Factor VIIa has a limited biological half-life in the blood stream, so it is generally desirable to frequently infuse smaller doses. The frequency of dosing is ordinarily every three to five hours. Less frequent doses can be employed in treating minor bleeding sites, e.g., small hematomas, while major bleeds such as traumatic wounds or surgical-dental procedures should require more frequent infusions.

Suitable factor VIIa compositions for use herein are well known. The methods of Kisiel et al., "Biochemistry" 16 (9): 4189–4193 (1977) or Broze and Majeurs, op. cit. can be used to produce factor VIIa suitable for use herein. The factor VIIa compositions produced by these methods contain residual activating protease (factors Xa or XIIa) which should be neutralized by separation from factor VIIa or by inhibition, for example by addition of an excess titer of anti-activating factor antiserum. While the latter technique is workable, it is preferred to purify the factor VIIa, thereby avoiding the addition of foreign agents to the composition.

Activating proteases may be separated from factor VIIa by insolubilization either before or after the activation. It is preferred to insolubilize the proteases before activation by cross linking them to insoluble, hydrophilic supports, e.g., cellulose, cross-linked dextrans or nylon, using cross-linking agents such as carbodiimide or cyanogen bromide in accordance with techniques generally known in the enzyme insolubilization art. Factor VIIa fails to exert any detectable feed-back proteolytic activity on such immobilized proteases.

Alternatively, factor VIIa can be separated from the activating protease by generally known protein purification techniques, e.g., electrophoresis, ultracentrifugation, immune affinity chromatography, ion exchange chromatography and the like.

The activation procedure of the foregoing authors may be further modified by the general procedure described in copending U.S. patent application Ser. No. 116,187. This procedure has as its foundation determining in advance of the completion of activation the conditions needed to achieve a factor VIIa composition of substantially predetermined activity. The method comprises (a) providing a starting material comprising factors VII and IX;

(b) substantially separating factor VII from factor IX;

(c) activating the factor VII-enriched fraction from step (b) by (i) selecting a condition which can be varied to control the degree of factor VII activation;

(ii) prior to the completion of activation, determining the magnitude of the condition needed to activate the factor VII to a predetermined degree of activation;

(iii) setting the condition to said magnitude;

(iv) conducting the activation of the factor VII in accordance with the condition; and (v) terminating the activation at the predetermined degree of activation.

Generally only one condition of the activation is permitted to vary, and this is usually the period of time that activation is allowed to proceed.

The magnitude of the selected condition is determined in one of two ways, or a combination of both. In the least preferred of the two methods, the condition is determined by removing aliquots of the composition after activation has been commenced, terminating the activation of each aliquot, determining the degree of activation of each aliquot and calculating the magnitude of the condition necessary to achieve a predetermined degree of activation of the fraction.

Alternatively, the condition magnitude may be determined by removing aliquots of the composition prior to activation, varying the condition among the aliquots, activating the aliquots in accordance with the condition set for each aliquot, terminating the activation, determining the degree of activation of each aliquot and calculating the magnitude of the condition necessary to achieve a predetermined degree of activation of the composition. This embodiment has the advantage that one cannot overrun the predetermined activation level, as could be done during the assay of aliquots withdrawn from a bulk lot which is simultaneously undergoing activation.

The degree of activation is generally monitored by following the increase in factor VII activity to a desired percentage increase, e.g., 15 times the starting activity. The method of Seligsohn et al., "Blood" 53 (5): 828-837 (1979) should be used for factor VII compositions which contain significant amounts of other clotting factors. This method is not an absolute measure of factor VIIa. Instead, it assays the change in ratio of factor VII to VIIa and is therefore a useful method for monitoring production of VIIa from the proenzyme.

EXAMPLE 1

The studies in this and the following examples were conducted on inbred dogs having hemophilia A. Hemostasis in such animals was followed by observing bleeding or clot formation at a 5×2×1.5 mm wound (template biopsy) made surgically on the gingiva superior to the maxillary cuspid. In normal dogs, bleeding from the wound closed in 5±2 minutes and sealed tightly with a concave contour without rebleeding. In contrast, hemophilic dogs formed an abnormal convex clot over the wound and rebled for several days if untreated. The hematocrit would drop by 2-10 percentage points in association with uncontrolled bleeding.

For all infusions the template biopsy and a post transfusion biopsy from the posterior of the mouth were fixed in neutral buffered formalin, divided and embedded in either paraffin or a methacrylate plastic and after sectioning stained for platelet plugs and for fibrin. No microvascular thrombosis was detected in the sections reviewed. This is consistent with the fact that no significant changes in either platelet counts or fibrinogen were observed.

The factor VIIa used in these studies was prepared by the method of Kisiel et al., op cit. from human plasma rather than bovine. The factor XIIa used in the activation was inhibited by the addition of rabbit antiserum raised against human factor XII and having an anti-factor XII titer of 50 µg. factor XII neutralized/ml antiserum by diisopropyl phosphorofluoridate. The purified factor VII prior to activation contained 3,250 units of factor VII/mg of protein (as measured by the method of Nemerson and Clyne, "J. Lab. Clin. Med." 83:301 [1974]). Benzamidine was removed from the factor VII by gel chromatography prior to activation. The factor increased the apparent factor VII activity approximately 10 fold after activation with factor XIIa when assayed using rabbit brain thromboplastin. VIIa thus generated was usually used within two hours, but could be used successfully within 72 hours if stored at 8° C. The concentration of factor VIIa was 240 µg/ml, and this concentration was used throughout the examples. The preparations used in Examples 1, 2 and 4-6 were believed to contain significant residual factor VII.

A 13.6 kg hemophilic dog was selected, a biopsy was performed on day 1, and another on days 7 and 8. On day 1 the dog was infused with unactivated factor VII at a dose of 1.8 µg/kg. Generally, in this example and those that follow, infusions were made no longer than 30 minutes after biopsy. Bleeding was not obvious clinically after this infusion but serial determinations of hemoglobin implied incomplete hemostasis. On day 7 another biopsy was done, and on this occasion 60 µg of factor VIIa was infused, or a dose of 4.4 µg/kg. Serial hemoglobin levels dropped in spite of this treatment, and clinically the bleeding continued. Therefore on day 8 a new biopsy was performed, and infusion was performed with a smaller dose of factor VIIa, that is 24 µg or 1.8 µg/kg. Serial hemoglobin assays on this date and clinical observation indicated cessation of bleeding with this dose of factor VIIa. Platelet counts during these three days of observation remained stable, although for unknown reasons the platelet counts on day 1 were higher than those on days 7 and 8.

EXAMPLE 2

This study was performed on a hemophilic dog with a weight of 14.1 kgs. On day 1 a biopsy was performed and the dog was injected with 24 µg of factor VIIa (1.7 µg/kg). This particular preparation of VIIa had not been treated with the anti-XII antibody and factor XIIa was therefore present. The bleeding did not cease either clinically or by serial determination of hematocrit. The antibody was added to the remainder of the preparation and the injection was repeated at 4:15 in the afternoon. Hemostasis then appeared to take place since the hematocrit was 37 on the afternoon on day 1 and 38 on the morning of day 2. On day 2 the biopsy was repeated and infusion of another 1.7 µg/kg of VIIa was repeated. Clinically the bleeding stopped within 10 minutes. Serial hematocrits were 31 and 32, and bleeding was clinically sporadic. Another 1.7 µg/kg of VIIa was given at 4 p.m. Very little bleeding appeared overnight and on day 3 the hematocrit was again 31%. A new biopsy was performed on day 3 with free bleeding obtained. 48 µg of factor VIIa was then infused, or a dose of 3.4 µg/kg. The drop in hematocrit over 24 hours indicated that this higher dose of VIIa had been less effective than the lower dose.

On day 4, clots were removed with gauze and all biopsy sites bled, especially the 24 hour wound. The dog was injected with 1.7 µg/kg of factor VIIa plus 100 microliters of standard rabbit brain thromboplastin. The injection was tolerated well, and the wounds began sealing at 10 minutes; however, observations and serial hematocrit determinations indicated that bleeding was continuing. At 2:45 the dog was injected with 0.85 µg/kg of factor VIIa. The bleeding appeared clinically to stop, and hemostasis appeared to remain stable through the study. Note however, that this injection was repeated at 9 p.m. on day 4, at 8 a.m. on day 5, at 8 a.m. on day 6 and at 8:30 a.m. on day 7.

EXAMPLE 3

Template gingival biopsies were performed on a 15.0 kg hemophilic dog on days 1, 2 and 3 under local anesthesia. Infusion on day 1 was with 0.16 µg of human factor VIIa/kg. There was no adverse reaction, as indeed there was no adverse reaction to any infusion with human factor VII or factor VIIa regardless of prior exposure throughout the study. In this case hemostasis appeared to be accomplished within 15 minutes, but rebleeding occurred within three or four hours of the infusion. Hematocrit was 35% late on the first day and 31% on the morning of the second day indicating some overnight bleeding. Infusion on day 2 was with 1.6 µg of factor VIIa/kg. Again, the bleeding appeared to stop, and on this occasion appeared to not recur until some time during the evening. The recurrence of bleeding was documented by a 24 hour drop in hematocrit from 31% to 25%. On day 3, infusion was performed with approximately 14 µg of factor VIIa/kg. On this occasion bleeding did not appear to cease clinically. The 24 hour drop in hematocrit on this occasion was from 25% to 15%. It was unclear whether the factor XIIa given along with the factor VIIa might not have been completely neutralized and thus might have triggered fibrinolysis. On day 4 the 24 hour wound was curetted and bleeding resumed. Bovine serum albumin was given as a placebo without cessation of the bleeding. 51 units of Proplex ® prothrombin complex/kg were infused and the bleeding appeared to recur in minor fashion overnight, although the 24 hour drop in hematocrit was only from 15-14%. On day 5, 48 units of factor VIII concentrate were infused or 32 units of factors VIII per kg. The bleeding ceased immediately and did not recur.

There was no consistent change on any of the days tested in apparent factor VIII as assayed either with factor VIII deficient canine substrate or factor VIII deficient human substrate. There was also no consistent change in activated partial thromboplastin time. The prothrombin time, however, did appear to change. On day 1 when 0.16 µg/kg of factor VIIa were infused, the prothrombin time shortening was striking and was evident within 15 minutes. It also was maintained for the entire day as was hemostasis. On the third day when even a larger dose was infused, the prothrombin time also shortened throughout the day, in spite of the fact that hemostasis was not achieved. Fibrinogen assays were also done on all samples, and showed no consistent change.

EXAMPLE 4

The next dog studied weighed 13.6 kgs. Biopsies were performed under local anesthesia on days 1, 2, 3 and 4 of the study. The dose of factor VIIa given on day 1 was 0.59 µg/kg. Clinically, the wound appeared sealed at 30 minutes, although the clot over the wound was convex and appeared fragile. Serial hematocrit determinations during the afternoon and the next morning revealed a hematocrit drop from only 38% to 36%. Serial particle counting with concomitant hemoglobin determinations also documented that very little blood was lost. The particle counting also indicated no significant change in platelet count. Therefore, hemostasis appeared to be achieved on this particular occasion in this animal with the dose at 0.59 µg/kg of factor VIIa. On day 2 the infusion was with 0.59 µg of unactivated factor VII/kg. In this case the hematocrit dropped, from a beginning value of 36, to 33 at 4 hours and 31 at 6 hours, and also to 28 on the following morning. Clinically there was also some bleeding during that time. Therefore, from these two days, it appeared that factor VIIa was hemostatically effective and factor VII was not. On day 3 the dog was again infused with 0.59 µg/kg of factor VIIa. The hematocrit prior to infusion was 28%, at 2 and 4 hours post infusion it was 29%. The wounds were oozing, however, so another dose of 0.59 µg/kg was given at 3 p.m. In spite of this the hematocrit dropped to 21% overnight. On day 4, infusion was with unactivated factor VII at 1.18 µg/kg. The hematocrit dropped from 21 preinfusion to 19 two hours post infusion to 16 five hours post infusion. At that point, the animal was infused with two vials of factor VIII concentrate (482 u, 35 u/kg) which appeared to control the bleeding. The hematocrit did not drop significantly over the next 24 hours, and the animal recovered without further treatment. As in previous experiments, the prothrombin time exhibited a mild shortening but none of the other assays seemed to change significantly. The prothrombin time shortening was seen with either activated or unactivated factor VII, but in vitro assays have implied that factor VII may be undergoing slow activation on storage in the absence of benzamidine even without the addition of factor XIIa.

EXAMPLE 5

The dog studied in this example had weighed 14.1 kgs. This dog underwent gingival biopsies on day 1 and day 2 of the study, and also on day 4. The beginning hematocrit was 54%. The injection on day 1 was with 1.42 µg of unactivated factor VII/kg. Hemostasis appeared to occur within 5 minutes, and was maintained for the first 30 minutes of observation; however, bleeding resumed at 3 p.m. and serial hematocrits indicated a beginning hematocrit of 54%, followed by a hematocrit of 52% at 4 hours and 47% at 6 hours. The hematocrit at 24 hours was 41% so this dose of factor VII clearly did not stop bleeding. On day 2, infusion was with factor VIIa (20 µg, 1.42 µg/kg). Again early hemostasis appeared the rule by observation, but serial determination of hematocrit documented a fall during the day from 41% to 31%, and a further fall to 26% by the next morning. Unactivated human factor VII was given on the third day in a dose twice that on day 1, i.e. 40 µg, 2.84 µg/kg. Clinically the bleeding appeared to slow down, and the 24 hour drop in hematocrit was only from 26% to 22%. On day 4 a new biopsy was performed and a dose of factor VIIa was given (40 µg, 2.84 µg/kg). This did not produce hemostasis, and the hematocrit dropped further to 16%. On this occasion, there was very little change in the prothrombin time when unactivated factor VII was used, but there was a significant drop when activated factor VII was used on days 2 and 4.

EXAMPLE 6

A 15.9 kg hemophilic dog had biopsies performed on days 1, 2, and 3. Infusion on day 1 was with 1.26 µg of factor VII/kg. Clinically the bleeding was intermittent, and by serial determinations of hemoglobin and hematocrit there was very little change in hemostasis. On day 2 factor VIIa was given in the dose of 1.26 µg/kg. Hemostasis was prompt, but serial determination of hemoglobin and hematocrit suggested, however, a slow loss of blood over the 24 hour period. On day 3, a new biopsy was performed and a placebo injection was given. This dog bled no further, and no additional infusions were administered.

It is concluded from the foregoing examples as a whole that factor VIIa is therapeutically useful in the treatment of clotting defects. While blood loss as evidenced by a fall in the hematocrit did occur after treatment with factor VIIa in some cases, the slope of the curve of a plot of the reduction in hematocrit was adjudged to be significantly less than that of control animals during the initial 3–6 hours after infusion.

I claim:

1. A method for treating a patient having a clotting factor defect, comprising administering to the patient an effective hemostatic amount of factor VIIa, which factor VIIa is uncontaminated by other activated blood clotting factors having sufficient activity alone to produce a hemostatic effect.

2. The method of claim 1 wherein the composition consists essentially of factors VII and VIIa.

3. The method of claim 1 wherein the hemostatic amount comprises about from 0.1 to 2.5 µg of factor VIIa/kg of body weight.

4. The method of claim 1 wherein the composition is administered by infusion.

5. The method of claim 1 wherein the composition is an aqueous solution.

6. The method of claim 5 wherein the factor VIIa is present in said solution at a concentration of about from 0.1 to 10.0 µg/ml.

7. The method of claim 1 wherein the composition comprises factor X.

8. The method of claim 1 wherein the composition is free of factors IXa and Xa.

9. The method of claim 1 wherein the patient is deficient in factor VIII activity.

10. The method of claim 1 wherein the patient's factor VIII activity is inhibited.

11. The method of claim 1 wherein the defect is manifest following chronic liver disease.

12. The method of claim 1 wherein the composition contains a stabilizer.

13. The method of claim 13 wherein the stabilizer is a protein at a concentration of greater than about 1 mg/ml.

14. The method of claim 14 wherein the protein is albumin.

15. The method of claim 1 wherein the amount of factor Xa in the composition is less than 1 unit/ml.

16. The method of claim 1 wherein the amount of factor IXa as measured by total factor IX activity minus factor IX precursor activity is less than about 15 units/ml.

17. The method of claim 1 wherein the defect is a clotting factor inhibitor.

18. A method for treating a patient having a clotting factor deficiency or inhibitor, comprising administering to the patient an effective hemostatic amount of a composition consisting essentially of factor VIIa, and wherein the factor VIIa is uncontaminated by other activated blood clotting factors having sufficient activity to produce a hemostatic effect.

19. In a method for treating a patient having a clotting factor deficiency or inhibitor wherein an activated prothrombin complex containing factors VIIa, IXa and Xa is administered to the patient, the improvement comprising administering factor VIIa to the patient substantially free of factors IXa and Xa.

* * * * *